US012527364B2

(12) United States Patent
Lock et al.

(10) Patent No.: US 12,527,364 B2
(45) Date of Patent: Jan. 20, 2026

(54) WEARABLE DEVICE CONFIGURED TO EVALUATE A BREAST AREA OF A USER AND PROVIDE A PREDICTION ASSOCIATED WITH THE BREAST AREA

(71) Applicant: COAPT LLC, Chicago, IL (US)

(72) Inventors: Blair Andrew Lock, Wilmette, IL (US); Levi John Hargrove, Chicago, IL (US)

(73) Assignee: HARLOCK CREATIVE LLC, Chicago, IL (US)

( * ) Notice: Subject to any disclaimer, the term of this patent is extended or adjusted under 35 U.S.C. 154(b) by 422 days.

(21) Appl. No.: 18/124,840

(22) Filed: Mar. 22, 2023

(65) Prior Publication Data

US 2023/0389623 A1 Dec. 7, 2023

Related U.S. Application Data

(60) Provisional application No. 63/347,842, filed on Jun. 1, 2022.

(51) Int. Cl.
*A41C 3/00* (2006.01)
*A61B 5/00* (2006.01)

(52) U.S. Cl.
CPC .......... *A41C 3/0064* (2013.01); *A61B 5/4312* (2013.01); *A61B 5/7275* (2013.01)

(58) Field of Classification Search
CPC .... A41C 3/0064; A61B 5/4312; A61B 5/7275
See application file for complete search history.

(56) References Cited

U.S. PATENT DOCUMENTS

2015/0177080 A1* 6/2015 Esposito .................. A61B 5/01 73/862.01
2020/0037949 A1* 2/2020 Subbhuraam ........ A61B 5/7275
2020/0069191 A1* 3/2020 Higia ................... A61B 5/6804
2022/0095996 A1 3/2022 Patterson

OTHER PUBLICATIONS

International Application No. PCT/US2023/015848, International Search Report and Written Opinion, mailed Dec. 12, 2024.
International Application No. PCT/US23/15848, International Search Report and Written Opinion, mailed Jun. 26, 2023.

* cited by examiner

*Primary Examiner* — Linda C Dvorak
*Assistant Examiner* — Abigail Bock
(74) *Attorney, Agent, or Firm* — MARSHALL, GERSTEIN & BORUN LLP

(57) ABSTRACT

A wearable device configured to evaluate a breast area of a user and provide a prediction associated with the breast area of the user is provided. The wearable device includes a garment insert detachably coupled to a garment designed for at least partial contact with the breast area of the user and sensors configured to collect data associated with the breast area of the user. The sensors may collect first breast data at a first time and second breast data at a second time, different from the first time. A breast area prediction may be generated based on comparing the first breast data to the second breast data, and may define an estimation of breast area risk for the user. A feedback indication may be provided to a user interface based on the breast area prediction, indicating whether the user should receive a breast area evaluation from a medical professional.

16 Claims, 4 Drawing Sheets

WEARABLE DEVICE CONFIGURED TO EVALUATE A BREAST AREA OF A USER AND PROVIDE A PREDICTION ASSOCIATED WITH THE BREAST AREA

CROSS-REFERENCE TO RELATED APPLICATIONS

The present disclosure claims priority to U.S. Provisional Patent Application No. 63/347,842, entitled "WEARABLE DEVICE CONFIGURED TO EVALUATE A BREAST AREA OF A USER AND PROVIDE A PREDICTION ASSOCIATED WITH THE BREAST AREA," and filed Jun. 1, 2022, the disclosure of which is incorporated by reference herein.

FIELD OF THE DISCLOSURE

The present disclosure generally relates to breast health and, more particularly, to a wearable device configured to evaluate a breast area of a user and provide a prediction associated with the breast area, and techniques associated therewith.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Currently, screening for breast cancer and other breast health conditions is typically done via yearly mammograms. However, there is currently no standardized screening for breast health that occurs more frequently than the yearly mammogram. Additionally, mammogram results regarding breast density can be inconclusive in terms of breast health for women who naturally have dense breast tissue.

Furthermore, mammograms require a doctor's visit, which can be inconvenient and expensive in some cases. Moreover, mammograms are uncomfortable for many women. Additionally, while breast self-exams can be done at any time with no cost to the individual, breast self-exams have not been shown to be effective in detecting cancer or improving survival rates for women who have breast cancer.

Accordingly, there is a need for wearable devices and related methods for evaluating a breast area of a user and for providing a prediction associated with the breast area, and techniques associated therewith.

SUMMARY

The present disclosure provides a wearable device and techniques associated therewith for evaluating a breast area (e.g., including the user's breast(s) and associated breast tissue, breast implant material, and/or the user's chest area) of a user and providing a prediction associated with the breast area of the user. The wearable device, which includes one or more sensors, may be inserted into a garment such as a standard brassiere, a sport brassiere, a swimsuit, a shirt, a dress, or any other garment designed for at least partial contact with the user's breast area. The sensors of the wearable device may capture data associated with the breast area of the user at various times, and this data may be analyzed to generate a user-specific breast area prediction.

The breast area prediction may be an estimation of breast area risk for the user (e.g., a risk of breast cancer, a risk of a breast implant rupturing, etc.), which may be generated based on changes in the data associated with the user that is captured by the sensors over time. A feedback indication may be provided via a user interface indicating the breast area prediction as well as a recommendation as to whether the user should receive a further breast area evaluation from a medical professional.

In particular, a garment insert that fits inside of a garment may use onboard sensors to make periodic measurements throughout the day and analyze the measurements to detect small changes. In some examples, based on these changes, the wearable device may determine an anomaly associated with the user's breast area, and may generate a recommendation that the user should receive a further breast area evaluation from a medical professional. The garment insert may be utilized with multiple types of compatible garments (including brassieres, sports brassieres, shirts, dresses, swimwear, etc.) and may be removable and interchangeable between multiple garments so that a user can use the insert with a second garment if a first garment is being washed, or based on different garments being used on different days.

Generally speaking, the garment insert may be worn by a user all day as the user wears the garment, and may take measurements throughout the day in order to measure changes over time (e.g., over the course of the day as well as over longer periods of time, such as over several days, over a month, over a year, etc.), for improved accuracy compared to one-time scans. The onboard sensors may include multiple types of sensors for increased accuracy. For instance, in an example, the sensors may measure temperature data in addition to another type of data. More specifically, with respect to various embodiments, a wearable device configured to evaluate a breast area of a user and provide a prediction associated with the breast area of the user is provided, the wearable device comprising: a garment insert configured to be detachably coupled to a garment, wherein the garment is designed for at least partial contact with the breast area of the user; one or more sensors configured to collect data associated with the breast area of the user; one or more processors communicatively coupled to the one or more sensors; a computer memory comprising computing instructions that when executed by the one or more processors, cause the one or more processors to: collect a first set of breast data sensed by the one or more sensors at a first time; collect a second set of breast data sensed by the one or more sensors at a second time, wherein the second time is different from the first time; generate a breast area prediction based on a comparison of the first set of breast data and the second set of breast data, wherein the breast area prediction defines an estimation of breast area risk for the user; and provide, based on the breast area prediction, a feedback indication to a user interface indicating whether the user should receive a breast area evaluation from a medical professional.

In additional embodiments, a computer-implemented method in a wearable device for evaluating a breast area of a user and providing a prediction associated with the breast area of the user is provided, the method comprising: collecting, by one or more sensors of a garment insert configured to be detachably coupled to a garment designed for at least partial contact with the breast area of the user, a first set of breast data associated with the breast area of the user at a first time; collecting, by the one or more sensors configured to collect data associated with the breast area of the user, a second set of breast data associated with the breast area of the user at a second time; generating, by one or more processors, a breast area prediction based on a comparison of the first set of breast data and the second set of breast data, wherein the breast area prediction defines an estimation of breast area risk for the user; and providing, by the one or more processors, based on the breast area prediction, a feedback indication to a user interface indicating whether the user should receive a breast area evaluation from a medical professional.

In still further embodiments, a tangible, non-transitory computer-readable medium is provided, storing instructions for evaluating a breast area of a user and providing a prediction associated with the breast area of the user that, when executed by one or more processors, cause the one or more processors to: collect a first set of breast data, associated with the breast area of the user, sensed by one or more sensors of a garment insert at a first time, the garment insert being configured to be detachably coupled to a garment designed for at least partial contact with the breast area of the user; collect a second set of breast data associated with the breast area of the user sensed by the one or more sensors at a second time; generate a breast area prediction based on a comparison of the first set of breast data and the second set of breast data, wherein the breast area prediction defines an estimation of breast area risk for the user; and provide, based on the breast area prediction, a feedback indication to a user interface indicating whether the user should receive a breast area evaluation from a medical professional.

The representative embodiments of the present systems and methods disclosed herein provide numerous advantages over commonly used methods, such as mammograms, in that the wearable device may be conveniently coupled to the user's clothing in order to conveniently collect large number of many different types of data points over time, without requiring a doctor visit and the discomfort, expense, or inconvenience associated therewith. Moreover, because the wearable device detects user-specific changes in the breast area, rather than flagging "unusual" breast tissue, the wearable device may detect changes in individual users that mammograms may be unable to detect, particular for users with naturally dense or otherwise atypical breast tissue. Accordingly, the present disclosure relates to improvement to other technologies or technical fields at least because the systems and methods disclosed herein may predict breast health risks at greater accuracy and efficiency than conventional techniques such as mammograms.

In accordance with the above, and with the disclosure herein, the present disclosure includes improvements in computer functionality or in improvements to other technologies at least because the disclosure describes that, e.g., a computing device, is improved where the intelligence or predictive ability of the computing device is enhanced by sensor data captured by multiple types of sensors of a wearable device worn by a user over time. A breast area prediction application, executing on the wearable device or on an associated computing device, is able to accurately predict, based on sensor data captured by multiple types of sensors of a wearable device worn by a user over time, a user-specific estimation of breast area risk for the user. That is, the present disclosure describes improvements in the functioning of the computer itself or "any other technology or technical field" because a wearable device or other computing device, is enhanced with sensor data captured by multiple types of sensors of the wearable device in order to accurately predict, detect, or determine user-specific breast area health risks, such as a risk of breast cancer based on changes in the specific user's breast area over time as the wearable device is worn day after day. This improves over the prior art at least because existing systems lack such user-specific predictive capabilities and are not able to capture these multiple types of sensor data over time from all-day wear in order to evaluate the breast area of the user and provide a prediction associated with the breast area of the user, as described herein.

For similar reasons, the present disclosure relates to improvement to other technologies or technical fields at least because the present disclosure describes or introduces improvements to computing devices in the field of breast health analysis, whereby the wearable devices and/or computing device improves the field of breast health analysis by evaluating a breast area of a user based on multiple types of sensor data captured by a wearable device and providing a prediction associated with the breast area of the user, as described herein.

Moreover, the present disclosure includes applying certain aspects or features, as described herein, with, or by the use of, a particular machine, e.g., a wearable device, which includes one or more sensors, that may be inserted into a garment such as a standard brassiere, a sport brassiere, a swimsuit, a shirt, a dress, or any other garment designed for at least partial contact with the user's breast area, and is configured to evaluate a breast area of a user and provide a prediction associated with the breast area of the user.

In addition, the present disclosure includes specific features other than what is well-understood, routine, conventional activity in the field, or adding unconventional steps that confine the claim to a particular useful application, e.g., evaluating a breast area of a user based on multiple types of sensor data captured by a wearable device and providing a prediction associated with the breast area of the user, as described herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The figures described below depict various aspects of the system and methods disclosed therein. It should be understood that each Figure depicts an embodiment of a particular aspect of the disclosed system and methods, and that each of the Figures is intended to accord with a possible embodiment thereof. Further, whenever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

DETAILED DESCRIPTION

Figure 1:
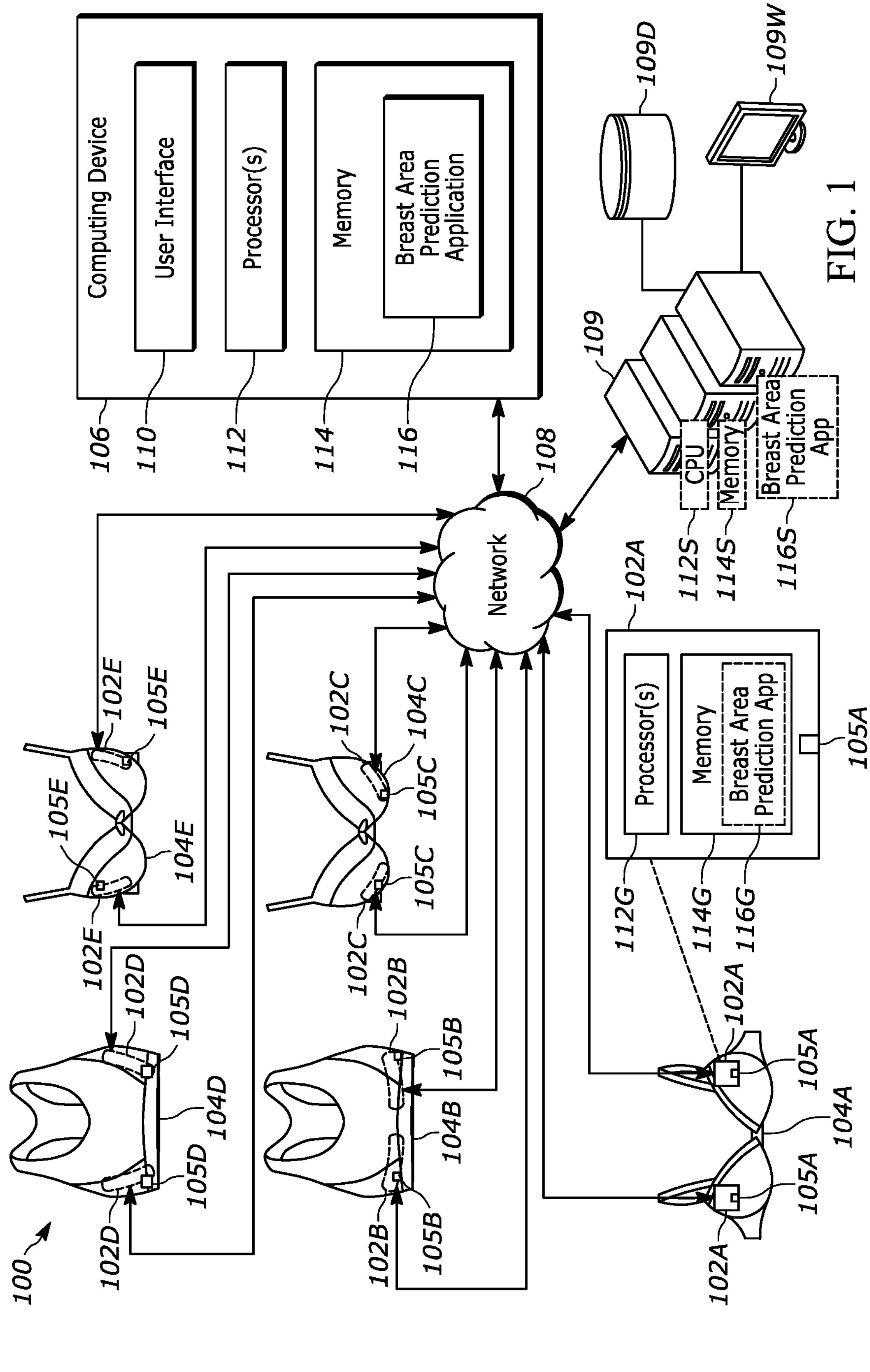
FIG. 1 is a block diagram of an example system for evaluating a breast area of a user and providing a prediction associated with the breast area of the user, in accordance with some examples provided herein.

While the systems and methods disclosed herein is susceptible of being embodied in many different forms, it is shown in the drawings and will be described herein in detail specific exemplary embodiments thereof, with the understanding that the present disclosure is to be considered as an exemplification of the principles of the systems and methods disclosed herein and is not intended to limit the systems and methods disclosed herein to the specific embodiments illustrated. In this respect, before explaining at least one embodiment consistent with the present systems and methods disclosed herein in detail, it is to be understood that the systems and methods disclosed herein is not limited in its application to the details of construction and to the arrangements of components set forth above and below, illustrated in the drawings, or as described in the examples. Methods and apparatuses consistent with the systems and methods disclosed herein are capable of other embodiments and of being practiced and carried out in various ways. Also, it is to be understood that the phraseology and terminology employed herein, as well as the abstract included below, are for the purposes of description and should not be regarded as limiting.

Referring now to the drawings, FIG. 1 is a block diagram of a system 100 for evaluating a breast area of a user (e.g., including the user's breast(s) and associated breast tissue, breast implant material, and/or the user's chest area) and providing a prediction associated with the breast area of the user, in accordance with some examples provided herein. The high-level architecture illustrated in FIG. 1 may include both hardware and software applications, as well as various data communications channels for communicating data between the various hardware and software components, as is described below.

The system 100 may comprise garment inserts 102A, 102B, 102C, 102D, and/or 102E (i.e., 102A-102E) configured to be detachably coupled to a respective garment 104A, 104B, 104C, 104D, and/or 104E (i.e., 104A-104E). The garments may comprise articles of clothing, underwear, or other wearable dress, such as brassieres, sports brassieres, shirts, dresses, swimwear, etc. The garment inserts are designed for at least partial contact with the breast area of a user. Although each of the one or more garment inserts 102A-102E are shown as comprising two inserts, a garment insert may comprise a single insert. In addition, each insert may be positioned on the garment in a different area or location of the garment other than as shown.

The one or more garment inserts 102A-102E may each include one or more respective sensors 105A-105E configured to collect data associated with the breast area of the user, and the garment inserts 102A-102E and/or the one or more sensors 105A-105E may be configured to communicate with a computing device 106, e.g., via a wired or wireless computer network 108, or via short-range communication techniques such as near-field communication (NFC), the Bluetooth™ communication standard, the Zigbee™ communication standard, WIFI communication standard, cellular phone communication standard, such as any of an LTE, 4G, or other cellular or mobile phone based standard, or any other suitable communication technique. Although one computing device 106 is shown as communicating with multiple garment inserts 102A-102E and/or multiple sensors 105A-105E in FIG. 1, in some examples each garment insert (or set of garment inserts) or each sensor (or set of sensors) may communicate with its own respective computing device 106.

In some aspects, the sensor data, as generated by any one or more of garment inserts 102A-102E and/or the one or more sensors 105A-105E, may be transmitted to one or more server(s) 109. In various aspects server(s) 109 comprise multiple servers, which may comprise multiple, redundant, or replicated servers as part of a server farm. In still further aspects, server(s) 109 may be implemented as cloud-based servers, such as a cloud-based computing platform. For example, server(s) 109 may be any one or more cloud-based platform(s) such as MICROSOFT AZURE, AMAZON AWS, or the like. Server(s) 109 may include one or more processor(s) 112*s* (e.g., CPUs) as well as one or more computer memories 114*s*.

Memories 114*s* may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. Memorie(s) 114*s* may store an operating system (OS) (e.g., Microsoft Windows, Linux, UNIX, etc.) capable of facilitating the functionalities, apps, methods, or other software as discussed herein. Memorie(s) 114*s* may also store a breast area prediction application (app) 116*s*, which may comprise or may be configured to access an artificial intelligence based model, such as a machine learning model, trained on the sensor data, as described herein. Additionally, or alternatively, sensor data, such as sensor data collected from any one or more of garment inserts 102A-102E and/or the one or more sensors 105A-105E, may also be stored in database 109*d*, which is accessible or otherwise communicatively coupled to server(s) 109. In addition, memories 114*s* may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. It should be appreciated that one or more other applications may be envisioned and that are executed by the processor(s) 112*s*. It should be appreciated that given the state of advancements of mobile computing devices, all of the processes functions and steps described herein may be present together on a mobile computing device (e.g., user computing device 106).

The processor(s) 112*s* may be connected to the memories 114*s* via a computer bus responsible for transmitting electronic data, data packets, or otherwise electronic signals to and from the processor(s) 112*s* and memories 114*s* in order to implement or perform the machine readable instructions, methods, processes, elements or limitations, as illustrated, depicted, or described for the various flowcharts, illustrations, diagrams, figures, and/or other disclosure herein.

Processor(s) 112*s* may interface with memory 114*s* via the computer bus to execute an operating system (OS). Processor(s) 112*s* may also interface with the memory 114*s* via the computer bus to create, read, update, delete, or otherwise access or interact with the data stored in memories 114*s* and/or the database 109*d* (e.g., a relational database, such as Oracle, DB2, MySQL, or a NoSQL based database, such as MongoDB). The data stored in memories 114*s* and/or database 109*d* may include all or part of any of the data or information described herein, including, for example, sensor data, which may be used as training data for artificial intelligence models, machine learning models, or the like, or as otherwise described herein.

Server(s) 109 may further include a communication component configured to communicate (e.g., send and receive) data via one or more external/network port(s) to one or more networks or local terminals, such as computer network 108 and/or terminal 109 (for rendering or visualizing) described herein. In some aspects, server(s) 109 may include a client-server platform technology such as ASP.NET, Java J2EE, Ruby on Rails, Node.js, a web service and/or online API, responsive for receiving and responding to electronic requests. The server(s) 109 may implement the client-server platform technology that may interact, via the computer bus, with the memories(s) 114*s* (including the applications(s), component(s), API(s), data, etc. stored therein) and/or database 109*d* to implement or perform the machine readable instructions, methods, processes, elements or limitations, as illustrated, depicted, or described for the various flowcharts, illustrations, diagrams, figures, and/or other disclosure herein.

In various aspects, the server(s) 109 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 108. In some aspects, computer network 108 may comprise a private network or local area network (LAN). Additionally, or alternatively, computer network 108 may comprise a public network such as the Internet.

Server(s) 109 may further include or implement an operator interface configured to present information to an administrator or operator and/or receive inputs from the administrator or operator. As shown in FIG. 1, an operator interface may provide a display screen (e.g., via terminal 109*w*). Server(s) 109 may also provide I/O components (e.g., ports, capacitive or resistive touch sensitive input panels, keys, buttons, lights, LEDs), which may be directly accessible via, or attached to, server(s) 109 or may be indirectly accessible via or attached to terminal 109*w*. According to some aspects, an administrator or operator may access the server 109 via terminal 109*w* to review information, make changes, manipulate sensor data, initiate training of artificial intelligence or machine learning models, and/or perform other functions as described herein.

In some aspects, server(s) 109 may perform the functionalities as discussed herein as part of a "cloud" network or may otherwise communicate with other hardware or software components within the cloud to send, retrieve, or otherwise analyze data or information described herein.

In general, a computer program or computer based product, application, or code (e.g., the model(s), such as AI models, or other computing instructions described herein) may be stored on a computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the processor(s) 112*s* (e.g., working in connection with the respective operating system in memories 114*s*) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, ActionScript, JavaScript, HTML, CSS, XML, etc.).

As shown in FIG. 1, server(s) 109 are communicatively connected, via computer network 108 to the one or more of garment inserts 102A-102E and/or one or more sensors 105A-105E. Additionally, server(s) 109 are communicatively connected, via computer network 108 to computing device 106. In some aspects, base stations, comprising cellular base stations, such as cell towers, may connect the garment inserts 102A-102E and/or the one or more sensors 105A-105E via wireless communications based on any one or more of various mobile phone standards, including the NMT, GSM, CDMA, UMMTS, LTE, 5G standards or the like. Additionally, or alternatively, base stations may comprise routers, wireless switches, or other such wireless connection points communicating to the garment inserts 102A-102E and/or the one or more sensors 105A-105E via wireless communications based on any one or more of various wireless standards, including by non-limiting example, IEEE 802.11a/b/c/g (WIFI), the BLUETOOTH standard, or the like.

Computing device 106 may comprise a mobile device and/or client device for accessing and/or communications with server(s) 109 and/or any one or more of garment inserts 102A-102E and/or the one or more sensors 105A-105E. Computing device 106 may comprise a user interface 110 (e.g., such as a display screen) one or more mobile processor(s) (e.g., processor(s) 112), memory 114. In various aspects, computing device 106 may comprise a mobile phone (e.g., a cellular phone), a tablet device, a personal data assistance (PDA), or the like, including, by non-limiting example, an APPLE iPhone or iPad device or a GOOGLE ANDROID based mobile phone or tablet.

In various aspects, user computing device 106 may implement or execute an operating system (OS) or mobile platform such as APPLE iOS and/or Google ANDROID operation system. User computing device 106 may comprise one or more processors (e.g., processor(s) 112) and/or one or more memories (e.g., memorie(s) 114) for storing, implementing, or executing computing instructions or code, e.g., a breast area prediction application 116, as described in various aspects herein. As shown in FIG. 1, breast area prediction application 116, or at least portions thereof, may also be stored locally on memory (e.g., memory 114) of a user computing device (e.g., computing device 106). Another portion of the breast area prediction application 116*s* app may be stored on server(s) 109 where breast area prediction application 116 executing on computing device 106 is communicatively coupled, via computer network 108, to breast area prediction application 116*s*. For example, breast area prediction application 116*s* may communicate via an API and may transmit sensor data our output, such as predictions or classifications as output by an artificial intelligence model. To facilitate such communications computer device 106 may comprise a wireless transceiver to receive and transmit wireless communications to and from base stations, which then may be transmitted and/or received via computer network 108 to server(s) 100.

With further reference to FIG. 1, in some aspects, the data collected by the one or more sensors 105A-105E may comprise one or more different types of sensors configured for collecting data comprising one or more of: temperature data; infrared data; ultrasound data; visible light based data; electromagnetic data; pressure data; inertial measurement unit (IMU) data; electromyography (EMG) data; electrocardiogram (ECG) data; electric impedance data; sweat based data; blood oxygen data; breast density data; fat content data; vibration data; magnetomyography (MaMG) data; mechanomyography (MeMG) data; and/or voice data. Such data can be captured at one or more different times across one or more time periods. The sensor data may be collected and transmitted to user device 106 and/or server(s) 109.

Moreover, in some examples, the data collected by the one or more sensors 105A-105E may include data associated with other sounds originating from the user, such as vocalizations, breathing, coughing, laughing, etc. In particular, in some examples, the data collected by the one or more sensors 105A-105E may include different instances of the same type of sound originating from the user, such as different instances of the user breathing (e.g., at different times), or different instances of the user vocalizing the same phoneme (e.g., at different times). For instance, changes in the pitch, tone, timbre, etc., of the sound originating from the user as it moves through the breast area of the user may be associated with changes in breast density, breast health, and/or other breast biological markers. In some aspects, a sensor data is collected when the user utters certain words, such as trigger words. In such aspects, the sensor data itself, causes vibrations and/or changes in the breast area and/or chest of the user. The trigger word may comprise, for example, a commonly spoken word, word(s), and/or phrases such as "yes," and/or "no." Additionally, or alternatively, the trigger word may comprise specific syllables, tones, and/or sounds (e.g., humming, whistling, etc.) of the user.

In some examples, the one or more sensors 105A-105E may be configured to operate in a "sleep" or "idle" mode until activated, e.g., by a user-controlled signal from the computing device 106, by determining that the garment (e.g., any one of garments 104A-104E) is in at least partial contact with the breast area of the user, by analyzing voice data originating from the user to determine that the user has said a trigger word, etc. For instance, the one or more sensors 105A-105E capturing other types of data may remain idle until a sensor 105A-105E capturing temperature data detects temperature indicating that a user is wearing the garment 104A-104E, and/or until a sensor 105A-105E capturing voice data detects the trigger word, which may activate the one or more sensors 105A-105E to begin capturing data, which may comprise the same and/or other types of data. In some aspects, a trigger word may comprise, for example, a commonly spoken word, word(s), and/or phrases such as "yes," and/or "no." Additionally, or alternatively, the trigger word may comprise specific syllables, tones, and/or sounds (e.g., humming, whistling, etc.) of the user.

Figure 2:
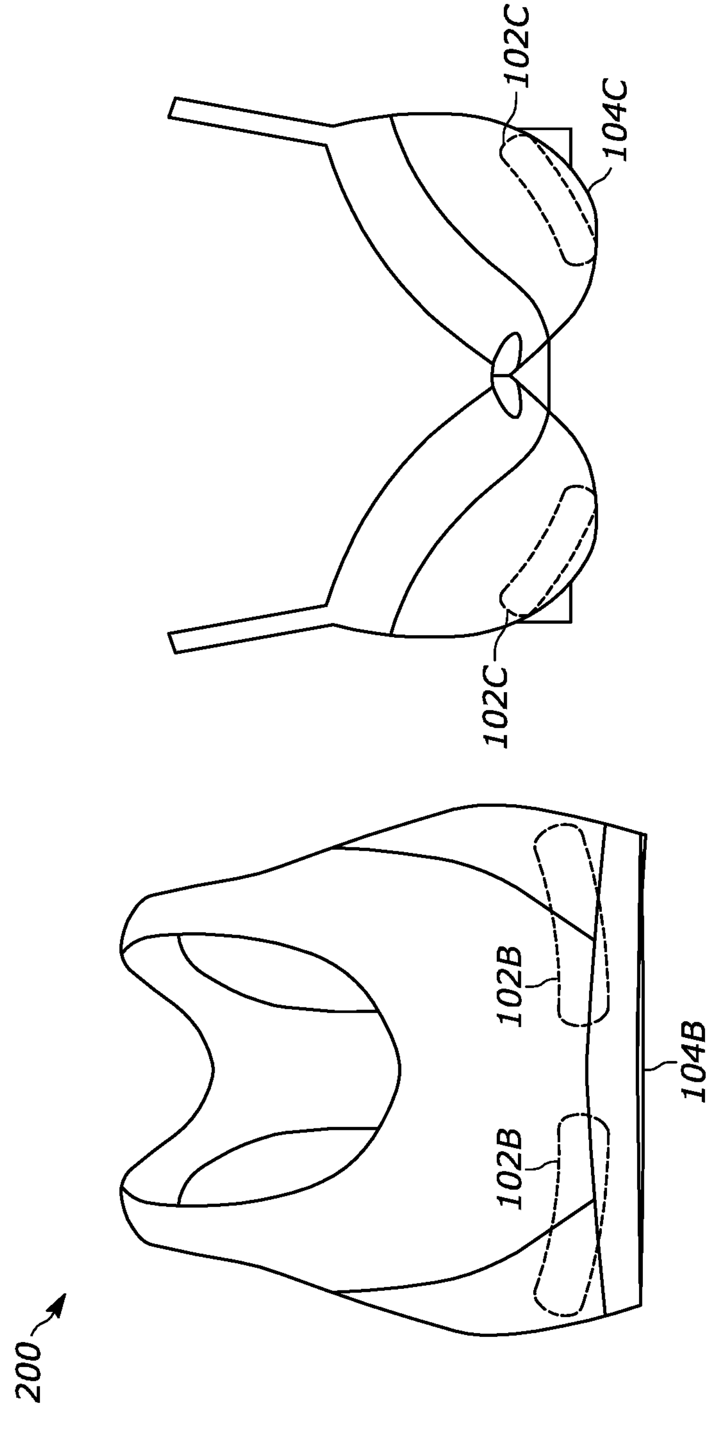
FIG. 2 illustrates example garments and example garment inserts of wearable devices for evaluating a breast area of a user and providing a prediction associated with the breast area of the user, in accordance with some examples provided herein.

FIG. 2 illustrates example garments 104B and 104C and example respective garment inserts 102B and 102C of wearable devices for evaluating a breast area of a user and providing a prediction associated with the breast area of the user, in accordance with some examples provided herein.

Figure 3:
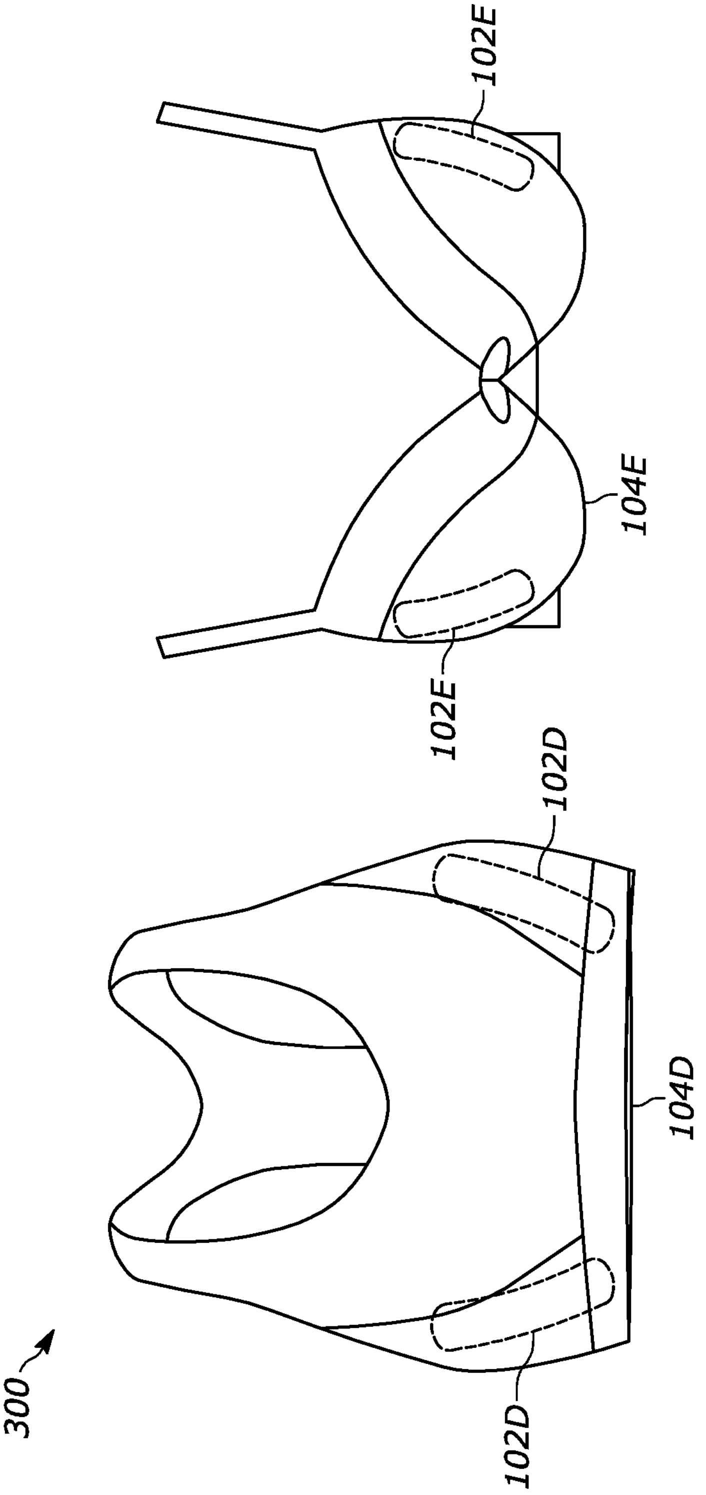
FIG. 3 further illustrates example garments and example garment inserts of wearable devices for evaluating a breast area of a user and providing a prediction associated with the breast area of the user, in accordance with some examples provided herein.

FIG. 3 further illustrates example garments 104D and 104E and example respective garment inserts 102D and 102E of wearable devices for evaluating a breast area of a user and providing a prediction associated with the breast area of the user, in accordance with some examples provided herein.

As shown, garments 104B and 104D is a sports undershirt and garments 104C and 104E is a brassiere. It should be understood, however, that any garment may be used where garment inserts (e.g., respective garment inserts 102B-102E) may be attached thereto. For example, as shown in FIGS. 2 and 3, there are multiple possible placement locations for the one or more garment inserts 102B-102E in various types of respective garments 104B-104E. For instance, in some examples, a one or more garments 104B-104E may include one or more pockets or pouches into which the respective garment insert(s) 102B-102E may be placed in order to capture data associated with the breast area of the user from the locations shown at FIGS. 2 and 3. Of course, the locations of the one or more garment inserts 102B-102E shown in FIGS. 2 and 3 are merely exemplary, and many other possible locations of garment inserts 102B-102E are possible in various aspects, including, for example garment inserts 102A as shown for FIG. 1. In addition, it should be understood, that in some aspects, as single garment insert (e.g., and not a pair of garment inserts as shown for FIG. 102B) may be used to collect sensor data of a single breast (e.g., breast tissue, breast implant material, etc.) or the breast's related area. In such aspects, the sensor data of the single garment insert is used for generating a breast area prediction associated with the single breast or otherwise the area of the garment insert analyzed by collection of sensor data for the single breast or its related area.

Generally speaking, the garment insert, such as any one or more of garment inserts 102A-102E, may be configured to be detachably coupled to a respective garment (e.g., garment(s) 104A-104E) designed for at least partial contact with the breast area of the user. For instance, the garment (e.g., any one or more of garment(s) 104A-104E) may be a brassiere (or a shirt, a swimsuit, a dress, etc.) including a flexible portion configured to conform to the breast area of the user. In some examples, the flexible portion may house one or more of the sensor(s) 105A-104E. Additionally, in some examples, the flexible portion may house one or more processors and/or one or more memories. For example, FIG. 1, shows an exploded view of a block diagram of garment insert 102A. The exploded view shows that a garment insert may comprise a processor 112*g* and a memory 114*g*. Processor 112*g* and memory 114*g* may be housed in a portion of the garment insert, such as a flexible portion of the garment insert. Processor 112*g* of the garment insert (e.g., garment insert 102A) may be communicatively coupled to the sensor(s) (e.g., sensor(s) 105A) for collecting sensor data, for determining time periods or time durations for collecting sensor data, and/or from communicating, transmitting, or receiving sensor data via computer network 108 to and/or from server(s) 109 and/or computing device 106. The sensor(s), (such as sensor 105A), may be positioned so as to be in contact with the breast of the user, subdermal to the breast of the user, and/or in a proximity to the breast of the user in various examples. Sensor data collected may differ based on placement of the sensors in relation to the breast of the user. In various aspects, the sensor data may be stored in memory 114*g*. In addition, in various aspects, memory 11*g* may store a breast area prediction app 116*g*, which may comprise a machine learning model, such as a breast area prediction model previously trained with sensor data of other individuals, and downloaded or installed on memory 114*g* of garment insert 102A. Additionally, or alternatively, a machine learning model, such as a breast area prediction model, may be trained with sensor data of a single user (e.g., user of the garment). Such training may occur overtime as the breast area prediction model is updated (e.g., automatically and/or continuously) with the user. The model may output a feedback indication that may indicate changes or deltas in the sensor data collected over time (e.g., between a first time and a second time) for the user's breast area as analyzed by sensor 105A. Such delta and/or change may indicate whether the user should receive a breast area evaluation from a medical professional.

In some examples, the one or more garment inserts 102A-102E may be configured to apply respective pressures for each of the one or more sensors 105A-105E as positioned with respect to the breast of the user based on detected movement of the breast of the user within or with respect to the garment. For instance, detecting the movement of the breast of the user within or with respect to the garment may include detecting a shift in position of the one or more sensors 105A-105E and/or a change in contact of the one or more sensors 105A-105E with the user's breast area. For instance, a change in contact of the one or more sensors 105A-105E with the user's breast area may be detected based on a change in contact from the one or more sensors 105A-105E with the user's breast area, a change in the force of contact of the one or more sensors 105A-105E with the user's breast area, etc. In some examples, this detected change of position of the one or more sensors 105A-105E may cause the moved sensor(s) 105A-105E to collect different data, e.g., such that a different amount of data is collected and/or such that a different fidelity/quality of data collected.

Referring back to FIG. 1, the computing device 106 may include a user interface 110, as well as one or more processors 112 and a memory 114. The user interface 110 may include a graphic user interface (GUI) configured to display the breast area prediction, the feedback indication, and/or the confidence level output. In some examples, the user interface 110 may include, e.g., a button, a switch, and/or one or more LED indicators. The memory 114 (e.g., volatile memory, non-volatile memory) may be accessible by the one or more processors 112 (e.g., via a memory controller). The one or more processors 112 may interact with the memory 114 to obtain, for example, computer-readable instructions stored in the memory 114.

Additionally, while the computing device 106 is shown as being separate from the garment inserts 102A-102E, in some examples the computing device 106, or one or more components thereof, may be incorporated into the one or more garment inserts 102A-102E or the garment 104A-104E itself, or attached thereto. For instance, the user interface 110, the processors 112, and/or the memory 114 may be incorporated into and/or communicate with the one or more garment inserts 102A-102E or the garment 104A-104E itself, or attached thereto, and may communicate with a user interface 110 of another computing device via the computer network 108 or any of the other communication techniques discussed above.

Moreover, in some examples, data captured by the one or more sensors 105A-105E may be transmitted to another remote processor (e.g., separate from processor(s) 112), which may be, e.g., a processor on a cloud computing system, a processor of a desktop computer of a medical professional, etc. For example, the remote processor may comprise processor(s) 112*s* of server(s) 109. In such aspects, the sensor data captured by sensors 105A-105E may be transmitted and stored in memory 114*s* and/or database 109*d*. It should be understood that the sensor data may be transmitted and/or received wirelessly and/or via wired communication (e.g., via the Internet and/or other communications) across computer network 108 to the remote processor(s), such as processor(s) 112 of computing device 106 and/or processor(s) 112*s* of server(s).

In any case, the computer-readable instructions stored in the memory 114 are configured to cause the one or more processors 112 to execute one or more applications, including a breast area prediction application 116. In addition, computer-readable instructions stored in the memory 114*s* are configured to cause the one or more processor(s) 112*s* to execute one or more applications, including a breast area prediction application 116*s*. Still further, computer-readable instructions stored in the memory 114*g* are configured to cause the one or more processor(s) 112*g* to execute one or more applications, including a breast area prediction application 116*g*. In some aspects, computer-readable instructions, such as computing instructions and/or applications executing at the server (e.g., server(s) 109), at a computing device (e.g., computing device 106), and/or on the garment insert (e.g., garment insert 102A) may be communicatively connected for transmitting and receiving sensor data, analyzing sensor data, outputting breast area prediction(s), and/or preforming other functions as described herein. For example, processor 112*g* of garment insert 112*g* may be communicatively coupled, via computer network 108, to one or more processors (e.g., processor(s) 112*s*) of server(s) 109. Processors 112*g* and 1112*s* may each be communicatively coupled to processor 112 of user device 106 via a computer network (e.g., computer network 108). In such aspects, a breast area prediction app may comprise a device app portion (e.g., breast area prediction app 116*g* configured to execute on the processor 112*g* of garment insert 102A), a server app portion (e.g., breast area prediction app 116*s*) configured to execute on the one or more processors of the server (e.g., server(s) 102), and a mobile app portion (e.g., breast area prediction app 116) configured to execute on one or more processors of a computing device, such as a mobile device (e.g., computing device 106). In such aspects, the server app portion, the mobile app portion, and/or the device app portion are configured to communicate with each other via computer network 108. The server app portion, the mobile app portion, and/or the device app portion may each be configured to implement, or partially implement, one or more of: (1) collecting a first set of breast data sensed by the one or more sensors at a first time; (2) collecting a second set of breast data sensed by the one or more sensors at a second time, wherein the second time is different from the first time; (3) generating a breast area prediction based on a comparison of the first set of breast data and the second set of breast data, wherein the breast area prediction defines an estimation of breast area risk for the user; and/or (4) providing, based on the breast area prediction, a feedback indication to a user interface indicating whether the user should receive a breast area evaluation from a medical professional. Additionally, or alternatively, the server app portion the mobile app portion, and/or the device app portion are configured to communicate to implement, or partially implement, computing instructions to perform one or more other methods or computing functions as described herein. Partial implementation may comprise a distributed app-network or code base, where each app portion comprises a portion of software instructions, code, or a machine learning model, and where each communicate via computer network 108 via an API (e.g., such as a RESTFUL API). For example, in some aspects, the garment insert 102A may comprise a device app portion (e.g., breast area prediction app 116*g*) that transmits sensor data to a server app portion (e.g., breast area prediction app 116*s*) on server 109. Server app portion (e.g., breast area prediction app 116*s*) may comprise a breast area prediction model stored in memory 114*s* of server 109. The breast area prediction model stored on server 109 outputs a feedback indication that may be transmitted to a user interface (e.g., user interface 110) indicating whether the user should receive a breast area evaluation from a medical professional.

Additionally, or alternatively, in other aspects, a single app may handle all functionality. For example, breast area prediction app 116*g* may comprise a machine learning model, such as breast area prediction model. In such aspects, the breast area prediction model receives sensor data as collected for a breast area of the user, and the breast area prediction model outputs a feedback indication to a user interface (e.g., user interface 110 or another user interface of the garment insert (not shown) indicating whether the user should receive a breast area evaluation from a medical professional. Such interaction can occur without sending sensor data or otherwise communicating to sever 109.

Executing the breast area prediction application 116 and/or breast area prediction application 116*s* may include analyzing the data captured by the sensors any one or more of 105A-105E, including sensor data captured over time, in order to generate a breast area prediction. The breast area prediction may comprise an output defining an estimation of breast area risk for the user, such as, e.g., a risk of breast cancer, or a risk of a breast implant rupturing. In particular, the breast area prediction application 116 and/or breast area prediction application 116*s* may compare data captured by any one or more of sensors 105A-105E at a first time to data captured by any one or more of sensors 105A-105E at a second time in order to generate the breast area prediction. For example, changes in any of the breast data captured by any one or more of sensors 105A-105E for a particular user may be associated with a change in breast density or breast biological markers for a particular user, and these types of changes may indicate a breast health risk for the particular user.

In some examples, the breast area prediction may include a confidence level output of the estimation of breast area risk. The confidence level output may be based on the amount of data and/or the signal quality of data of the breast data collected by the any one or more of sensors 105A-105E. For instance, the confidence level output may be higher when more breast data is collected by any one or more of sensors 105A-105E, and may be lower when less breast data is collected by any one or more of sensors 105A-105E. Furthermore, the confidence level output may be higher when the signal quality of the breast data collected by any one or more of sensors 105A-105E is higher, and may be lower when the signal quality of the breast data collected by any one or more of sensors 105A-105E is lower.

In various aspects, executing the breast area prediction application 116 and/or breast area prediction application 116*s* comprises training a machine learning model to generate a breast area prediction based on data captured by one or more sensors (e.g., any one or more of 105A-105E). Additionally, or alternatively, executing the breast area prediction application 116 and/or breast area prediction application 116*s* comprises utilizing a previously trained machine learning model to generate and/or output a breast area prediction based on data captured by the one or more sensors 105A-105E. For instance, a machine learning model may be trained with data from one or more sensors (e.g., one or more of sensors 105A-105E) of a plurality of users to generate a machine learning based breast area prediction model. Once trained, the breast area prediction model may then be provided new sensor data (e.g., sensor data of garment insert(s) 102A) to output a breast area prediction of a specific user (e.g., the user wearing garment 104A). In this way, the senor data collected from multiple users is used to define or output, via the breast area prediction model, a feedback indication to a user interface indicating whether the user should receive a breast area evaluation from a medical professional, or to analyze breast tissue, breast implant material, and/or breast biological markers of the multiple users upon which the breast area prediction model was trained. For instance, in some examples, the breast area prediction application 116 and/or or breast area prediction application 116*s* may train the breast area prediction model (e.g., a machine learning model) using data captured by respective sensors 105A, 105B, 105C, 105D, and/or 105E associated with users of respective garments 104A, 104B, 105C, 105D, and/or 105E. Of course, while five such garments 104A-104E are shown in FIG. 1, sensor data captured by sensors of any number of garments (e.g., thousands or tens of thousands of garments) may be used to train the machine learning model.

Additionally, or alternatively, a machine learning model, may be trained with sensor data collected of a single specific and/or individual user. In such aspects, training the breast area prediction model comprises generating a new model and/or updating a previously trained baseline machine learning model to generate and/or output a breast area prediction based on data captured by sensor(s) (e.g., sensors 105A) of a specific user's garment inserts. For instance, a machine learning model, such as breast area prediction model, may be trained with data from sensors (e.g., one or more of sensors 105A) of a single user to generate a machine learning based breast area prediction model specific to that user. Once trained, the breast area prediction model of the specific user may then be provided new sensor data (e.g., sensor data collected by sensor(s) 105A of garment insert(s) 102A) to output a breast area prediction of a specific user (e.g., the user wearing garment 104A). In this way, the senor data collected from the single user may be used to define, via the breast area prediction model of the specific user, a feedback indication to a user interface indicating whether the user should receive a breast area evaluation from a medical professional, or to analyze the breast tissue of the user, breast implant material, or breast biological markers of the user upon which the breast area prediction model was trained. For instance, in some examples, the breast area prediction application 116*g* may train the breast area prediction model (e.g., a machine learning model) of the specific user using data captured by sensor(s) (e.g., sensor 105A) of the user's specific garment insert(s) (e.g., garment insert(s) 102A). Such training may occur overtime as the breast area prediction model is updated (e.g., automatically and/or continuously) with the user. The model may output a feedback indication that may indicate changes or deltas in the sensor data collected over time (e.g., between a first time and a second time) for the user's breast area as analyzed by sensor 105A. Such delta and/or change may indicate whether the user should receive a breast area evaluation from a medical professional. In some aspects, training and execution of the model can occur on the garment insert (e.g., garment insert 102A) alone, without interaction from server(s) 109 and/or computing device 106. Additionally, or alternatively, app portions, located on sever(s) 109, computing device 106, and/or garment insert 102A may distribute training, execution, and/or output of breast area prediction model as described herein.

In various aspects, the breast area prediction model comprises a machine learning program or algorithm that may be trained by and/or employ a neural network, which may be a deep learning neural network, or a combined learning module or program that learns in one or more features or feature datasets (e.g., breast data) in particular area(s) of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. In some embodiments, the artificial intelligence and/or machine learning based algorithms used to train the breast area prediction model may comprise a library or package executed on the server(s) 109 and/or computing device 106 (or other computing devices not shown in FIG. 1). For example, such libraries may include the TENSORFLOW based library, the PYTORCH library, and/or the SCIKIT-LEARN Python library.

Machine learning may involve identifying and recognizing patterns in existing data (such as training a model based on sensor data measuring breasts of a plurality of users, and breast health data, breast biological markers, breast cancer rates, etc., from those plurality of users) in order to facilitate making predictions or identification for subsequent data (such as using the breast area prediction model on new breast data of a new or specific user or individual in order to determine a user-specific breast health prediction, e.g., a breast area prediction as described herein).

Machine learning model(s) may be created and trained based upon example data (e.g., "training data") inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

Furthermore, executing the breast area prediction application 116 may further include providing a feedback indication via the user interface 110 indicating whether the user should receive a breast area evaluation from a medical professional, based on the breast area prediction. That is, the feedback indication may indicate whether the individual should seek further evaluation from a medical professional. Additionally, or alternatively, the feedback indication may indicate that further evaluation from a medical professional is and/or is not required. For instance, in some examples, the breast area prediction may be a numerical prediction (e.g., 75% risk, 5/10 risk, etc.) or otherwise a scaled prediction (e.g., orange level risk in a color scale, A-level risk in an alphabetical scale, each indicating a degree of risk or severity of breast issues). The breast area prediction application 116 may provide an indication that the user should receive a breast area evaluation from a medical professional based on the breast area prediction being greater than a threshold level (e.g., greater than 60% risk, greater than 5/10 risk, greater than yellow risk, greater than C-level risk, etc.), and/or may provide an indication that the breast area evaluation is not required based on the breast area prediction being lower than the threshold level. The feedback indication may be provided to, e.g., the user, a medical professional, and/or another authorized user (i.e., different from the user themselves).

The feedback indication may include, e.g., a visual stimulus, an auditory stimulus, and/or a tactile stimulus provided by the one or more garment inserts 102A-102E and/or the computing device 106 in various examples. For instance, a visual stimulation may be a message, an application notification (e.g., provided by the breast area prediction application 106 of the computing device 106, another application stored on the memory 114 of the computing device 106, and/or another application of another computing device), a text message, or an email. An auditory stimulus may include an audible alert, such as from a speaker of the user interface 110. Additionally, a tactile stimulus may include a vibration from vibrator, e.g., of the one or more garment inserts 102A-102E and/or of the computing device 106.

Furthermore, in some examples, the computer-readable instructions stored on the memory 114 may include instructions for carrying out any of the steps of the method 400, which comprises an algorithm configured to execute on processor(s) 112*s* and/or 112, and which is described in greater detail below with respect to FIG. 4.

Figure 4:
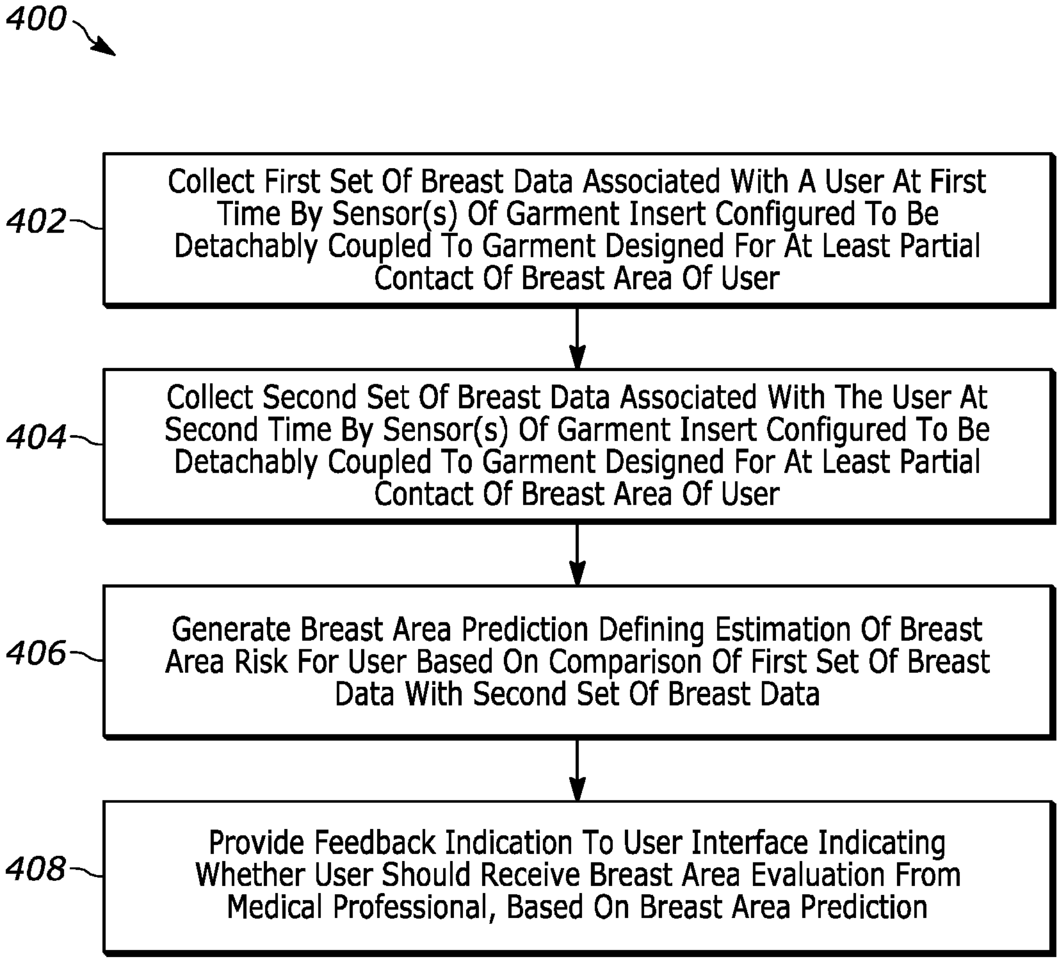
FIG. 4 is a flow diagram of an example method for evaluating a breast area of a user and providing a prediction associated with the breast area of the user, as may be implemented in the system of FIG. 1, in accordance with some examples provided herein.

FIG. 4 is a flow diagram of an example method 400 for evaluating a breast area of a user and providing a prediction associated with the breast area of the user, as may be implemented in the system of FIG. 1, in accordance with some examples provided herein. One or more steps of the method 400 may be implemented as a set of instructions stored on a computer-readable memory (e.g., memory 114 and/or 114*s*) and executable on one or more processors (e.g., processor(s) 112 and/or processor(s) 112*s*).

Block 402 may include collecting, by one or more sensors (e.g., sensor(s) 105A) of a garment insert (e.g., 102A) configured to be detachably coupled to a garment (e.g., garment 104A) designed for at least partial contact with the breast area of the user. This may be, for example, a breast area of or near the garment insert(s) as shown for garment insert(s) 102A. A first set of breast data is associated with the breast area of the user at a first time.

Block 404 may include collecting, by the one or more sensors (e.g., sensor(s) 105A) configured to collect data associated with the breast area of the user, a second set of breast data associated with the breast area of the user at a second time.

Block 406 may include generating, by one or more processors (e.g., processor(s) 112 and/or processor(s) 112*s*), a breast area prediction based on a comparison of the first set of breast data and the second set of breast data. In such aspects, the breast area prediction defines an estimation of breast area risk for the user.

Block 408 may include providing, by the one or more processors (e.g., processor(s) 112 and/or processor(s) 112*s*), based on the breast area prediction, a feedback indication to a user interface (e.g., user interface 110) indicating whether the user should receive a breast area evaluation from a medical professional.

Aspects of the Disclosure

1. A wearable device configured to evaluate a breast area of a user and provide a prediction associated with the breast area of the user, the wearable device comprising: a garment insert configured to be detachably coupled to a garment, wherein the garment is designed for at least partial contact with the breast area of the user; one or more sensors configured to collect data associated with the breast area of the user; one or more processors communicatively coupled to the one or more sensors; a computer memory comprising computing instructions that when executed by the one or more processors, cause the one or more processors to: collect a first set of breast data sensed by the one or more sensors at a first time; collect a second set of breast data sensed by the one or more sensors at a second time, wherein the second time is different from the first time; generate a breast area prediction based on a comparison of the first set of breast data and the second set of breast data, wherein the breast area prediction defines an estimation of breast area risk for the user; and provide, based on the breast area prediction, a feedback indication to a user interface indicating whether the user should receive a breast area evaluation from a medical professional.
2. The wearable device of aspect 1, wherein the breast area prediction comprises a confidence level output of the estimation of breast area risk, and where the confidence level output is based on an amount of data and a signal quality of data of one or more of: the first set of breast data or the second set of breast data.
3. The wearable device of any one of aspects 1 or 2, wherein the garment is a brassiere, and wherein the brassiere comprises a flexible portion configured to conform to the breast of the user, and wherein the flexible portion houses at least one of the one or more sensors, and at least one of the one or more processors.
4. The wearable device of any one of aspects 1-3, wherein the one or more sensors are positioned at least at one of: in contact with the breast of the user, subdermal to the breast of the user, or in a proximity to the breast of the user.
5. The wearable device of any one of aspects 1-4, wherein the garment insert is configured to apply one or more pressures for each of the one or more sensors as positioned with respect to the breast of the user, and wherein the one or more pressures applied is based on detected movement of the breast of the user within or with respect to the garment.

6. The wearable device of aspect 5, wherein a change of position of a moved sensor of the one or more sensors causes the moved sensor to collect different data.
7. The wearable device of any one of aspects 1-6, wherein the breast data comprises of at least one of: temperature data; infrared data; ultrasound data; visible light based data; electromagnetic data; pressure data; inertial measurement unit (IMU) data; electromyography (EMG) data; electrocardiogram (ECG) data; electric impedance data; sweat based data; blood oxygen data; breast density data; fat content data; vibration data; or voice data.
8. The wearable device of any one of aspects 1-7, wherein the breast data comprises data of the user comprising sound originating from the user, wherein the first set of breast data comprises a first sound as captured at the first time, and wherein the second set of breast data comprises a second sound as captured at the second time, and wherein the first sound is different from the second sound.
9. The wearable device of aspect 8, wherein the first sound and the second sound are captured during respective first and second instances of the user vocalizing the same phoneme.
10. The wearable device of aspect 8, wherein collection of the first set of breast data and the second set of breast data is activated by the one or more processors when the user voices a trigger word.
11. The wearable device of any one of aspects 1-10, wherein the user interface comprises a graphic user interface (GUI) configured to display at least one of the breast area prediction, the feedback indication, or a confidence level output.
12. The user interface of any one of aspects 1-11, wherein the user interface comprises at least one of: a button, a switch, or one or more LED indicators.
13. The wearable device of any one of aspects 1-12, wherein at least one of the one or more processors comprise a remote processor communicatively coupled to the garment insert, and wherein the first set of breast data and the second set of breast data is transmitted across a computer network to the remote processor.
14. The wearable device of any one of aspects 1-13, wherein the breast area prediction is output by a machine learning model previously trained on training breast data, wherein the training breast data comprises sensor data as collected from a plurality of users and that defines breast tissue, breast implant material, or breast biological markers of the plurality of users.
15. The wearable device of any one of aspects 1-14, wherein the one or more sensors are configured to initiate collecting data associated with the breast area of the user based on determining that the garment is in at least partial contact with the breast area of the user.
16. A computer-implemented method in a wearable device for evaluating a breast area of a user and providing a prediction associated with the breast area of the user, the method comprising: collecting, by one or more sensors of a garment insert configured to be detachably coupled to a garment designed for at least partial contact with the breast area of the user, a first set of breast data associated with the breast area of the user at a first time; collecting, by the one or more sensors configured to collect data associated with the breast area of the user, a second set of breast data associated with the breast area of the user at a second time; generating, by one or more processors, a breast area prediction based on a comparison of the first set of breast data and the second set of breast data, wherein the breast area prediction defines an estimation of breast area risk for the user; and providing, by the one or more processors, based on the breast area prediction, a feedback indication to a user interface indicating whether the user should receive a breast area evaluation from a medical professional.

17. A tangible non-transitory computer-readable medium storing instructions for evaluating a breast area of a user and providing a prediction associated with the breast area of the user that, when executed by one or more processors, cause the one or more processors to: collect a first set of breast data, associated with the breast area of the user, sensed by one or more sensors of a garment insert at a first time, the garment insert being configured to be detachably coupled to a garment designed for at least partial contact with the breast area of the user; collect a second set of breast data associated with the breast area of the user sensed by the one or more sensors at a second time; generate a breast area prediction based on a comparison of the first set of breast data and the second set of breast data, wherein the breast area prediction defines an estimation of breast area risk for the user; and provide, based on the breast area prediction, a feedback indication to a user interface indicating whether the user should receive a breast area evaluation from a medical professional.

ADDITIONAL CONSIDERATIONS

The methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

What is claimed is:

1. A wearable device configured to evaluate a breast area of a user and provide a prediction associated with the breast area of the user, the wearable device comprising:

a garment insert configured to be detachably coupled to a garment, wherein the garment is designed for at least partial contact with the breast area of the user;

one or more sensors configured to collect breast data associated with the breast area of the user, wherein the breast data comprises of at least one of: infrared data, ultrasound data, visible light based data, electromagnetic data, pressure data, inertial measurement unit (IMU) data, electromyography (EMG) data, electrocardiogram (ECG) data, electric impedance data, sweat based data, blood oxygen data, breast density data, fat content data, vibration data, magnetomyography (MaMG) data, mechanomyography (MeMG) data, or voice data;

one or more processors communicatively coupled to the one or more sensors; and a computer memory comprising computing instructions that when executed by the one or more processors, cause the one or more processors to:

collect a first set of breast data sensed by the one or more sensors at a first time;

collect a second set of breast data sensed by the one or more sensors at a second time, wherein the second time is different from the first time;

generate a breast area prediction based on a comparison of the first set of breast data and the second set of breast data, wherein the breast area prediction defines an estimation of breast area risk for the user; and provide, based on the breast area prediction, a feedback indication to a user interface indicating whether the user should receive a breast area evaluation from a medical professional.

2. The wearable device of claim 1, wherein the breast area prediction comprises a confidence level output of the estimation of breast area risk, and where the confidence level output is based on an amount of data and a signal quality of data of one or more of: the first set of breast data or the second set of breast data.

3. The wearable device of claim 1, wherein the garment is a brassiere, and wherein the brassiere comprises a flexible portion configured to conform to the breast area of the user, and wherein the flexible portion houses at least one of the one or more sensors, and at least one of the one or more processors.

4. The wearable device of claim 1, wherein the one or more sensors are positioned at least at one of: in contact with the breast area of the user, subdermal to the breast area of the user, or in a proximity to the breast area of the user.

5. The wearable device of claim 1, wherein the user interface comprises a graphic user interface (GUI) configured to display at least one of the breast area prediction, the feedback indication, or a confidence level output.

6. The wearable device of claim 1, wherein the user interface comprises at least one of: a button, a switch, or one or more LED indicators.

7. The wearable device of claim 1, wherein at least one of the one or more processors comprise a remote processor communicatively coupled to the garment insert, and wherein the first set of breast data and the second set of breast data is transmitted across a computer network to the remote processor.

8. The wearable device of claim 1, wherein the breast area prediction is output by a machine learning model previously trained on training breast data, wherein the training breast data comprises sensor data as collected from a plurality of users and that defines breast tissue, breast implant material, or breast biological markers of the plurality of users.

9. The wearable device of claim 1, wherein the one or more sensors are configured to initiate collecting data associated with the breast area of the user based on determining that the garment is in at least partial contact with the breast area of the user.

10. The wearable device of claim 1, wherein the garment insert is configured to apply one or more pressures for each of the one or more sensors as positioned with respect to the breast area of the user, and wherein the one or more pressures applied is based on detected movement of the breast area of the user within or with respect to the garment.

11. The wearable device of claim 10, wherein a change of position of a moved sensor of the one or more sensors causes the moved sensor to collect different data.

12. The wearable device of claim 1, wherein the breast data comprises data of the user comprising sound originating from the user, wherein the first set of breast data comprises a first sound as captured at the first time, and wherein the second set of breast data comprises a second sound as captured at the second time, and wherein the first sound is different from the second sound.

13. The wearable device of claim 12, wherein the first sound and the second sound are captured during respective first and second instances of the user vocalizing a same phoneme.

14. The wearable device of claim 12, wherein collection of the first set of breast data and the second set of breast data is activated by the one or more processors when the user voices a trigger word.

15. A computer-implemented method in a wearable device for evaluating a breast area of a user and providing a prediction associated with the breast area of the user, the computer-implemented method comprising:

collecting, by one or more sensors of a garment insert configured to be detachably coupled to a garment designed for at least partial contact with the breast area of the user, a first set of breast data associated with the breast area of the user at a first time, wherein breast data comprises of at least one of: infrared data, ultrasound data, visible light based data, electromagnetic data, pressure data, inertial measurement unit (IMU) data, electromyography (EMG) data, electrocardiogram (ECG) data, electric impedance data, sweat based data, blood oxygen data, breast density data, fat content data, vibration data, magnetomyography (MaMG) data, mechanomyography (MeMG) data, or voice data;

collecting, by the one or more sensors, a second set of breast data associated with the breast area of the user at a second time;

generating, by one or more processors, a breast area prediction based on a comparison of the first set of breast data and the second set of breast data, wherein the breast area prediction defines an estimation of breast area risk for the user; and providing, by the one or more processors, based on the breast area prediction, a feedback indication to a user interface indicating whether the user should receive a breast area evaluation from a medical professional.

16. A tangible non-transitory computer-readable medium storing instructions for evaluating a breast area of a user and providing a prediction associated with the breast area of the user that, when executed by one or more processors, cause the one or more processors to:

collect a first set of breast data, associated with the breast area of the user, sensed by one or more sensors of a garment insert at a first time, the garment insert being configured to be detachably coupled to a garment designed for at least partial contact with the breast area of the user, wherein breast data comprises of at least one of: infrared data, ultrasound data, visible light based data, electromagnetic data, pressure data, inertial measurement unit (IMU) data, electromyography (EMG) data, electrocardiogram (ECG) data, electric impedance data, sweat based data, blood oxygen data, breast density data, fat content data, vibration data, magnetomyography (MaMG) data, mechanomyography (MeMG) data, or voice data;

collect a second set of breast data associated with the breast area of the user sensed by the one or more sensors at a second time;

generate a breast area prediction based on a comparison of the first set of breast data and the second set of breast data, wherein the breast area prediction defines an estimation of breast area risk for the user; and provide, based on the breast area prediction, a feedback indication to a user interface indicating whether the user should receive a breast area evaluation from a medical professional.

* * * * *